United States Patent
Ishihara

(10) Patent No.: US 10,569,133 B2
(45) Date of Patent: Feb. 25, 2020

(54) MEASUREMENT SYSTEM AND MEASUREMENT METHOD

(71) Applicant: BRIDGESTONE SPORTS CO., LTD., Tokyo (JP)

(72) Inventor: Tomotaka Ishihara, Chichibu (JP)

(73) Assignee: Bridgestone Sports Co., Ltd., Tokyo (JP)

( * ) Notice: Subject to any disclaimer, the term of this patent is extended or adjusted under 35 U.S.C. 154(b) by 212 days.

(21) Appl. No.: 15/406,035

(22) Filed: Jan. 13, 2017

(65) Prior Publication Data

US 2017/0239519 A1    Aug. 24, 2017

(30) Foreign Application Priority Data

Feb. 23, 2016   (JP) .................................. 2016-032417

(51) Int. Cl.
*A63B 24/00* (2006.01)
*A63B 69/36* (2006.01)

(52) U.S. Cl.
CPC ...... *A63B 24/0003* (2013.01); *A63B 69/3667* (2013.01); *A63B 2208/0204* (2013.01); *A63B 2220/50* (2013.01)

(58) Field of Classification Search
CPC ............ A63B 24/0003; A63B 69/3667; A63B 2208/0204; A63B 2220/50; A61B 5/1121; A61B 5/22
USPC .................................................. 473/269, 131
See application file for complete search history.

(56) References Cited

U.S. PATENT DOCUMENTS

| | | | |
|---|---|---|---|
| 8,142,300 B2 | 3/2012 | Iwatsubo et al. | |
| 8,475,300 B2 | 7/2013 | Ueda | |
| 2006/0052173 A1 | 3/2006 | Telford | |
| 2012/0179385 A1* | 7/2012 | Nagashima | A63B 69/0002 702/19 |
| 2012/0316004 A1* | 12/2012 | Shibuya | A63B 24/0006 473/212 |
| 2014/0100048 A1 | 4/2014 | Ota et al. | |
| 2014/0100049 A1 | 4/2014 | Ota et al. | |
| 2014/0342844 A1* | 11/2014 | Mooney | G06K 9/00342 473/266 |
| 2015/0142374 A1 | 5/2015 | Shibuya | |

FOREIGN PATENT DOCUMENTS

| | | |
|---|---|---|
| JP | 03-012183 A | 1/1991 |
| JP | 2008-539856 A | 11/2008 |
| JP | 2009-005760 A | 1/2009 |
| JP | 2009-297240 A | 12/2009 |
| JP | 3155758 U | 12/2009 |
| JP | 2011-502602 A | 1/2011 |
| JP | 2011-030761 A | 2/2011 |

(Continued)

*Primary Examiner* — Omkar A Deodhar
*Assistant Examiner* — Wei Lee
(74) *Attorney, Agent, or Firm* — Sughrue Mion, PLLC

(57) ABSTRACT

A measurement system includes a first measurement unit configured to measure floor reaction forces of golfer's left and right legs, a second measurement unit that is attached to the upper body of a golfer and configured to measure an angular velocity of the golfer, and a processing unit. The processing unit calculates, based on measurement results of the first measurement unit and the second measurement unit, a first energy which is a kinetic energy of the golfer during a swing.

12 Claims, 7 Drawing Sheets

(56) References Cited

FOREIGN PATENT DOCUMENTS

| | | |
|---|---|---|
| JP | 2013-090862 A | 5/2013 |
| JP | 2014-073313 A | 4/2014 |
| JP | 2014-073314 A | 4/2014 |
| JP | 2014-530047 A | 11/2014 |
| JP | 2015-096105 A | 5/2015 |
| WO | 2006/120658 A1 | 11/2006 |
| WO | 2009/060010 A2 | 5/2009 |
| WO | 2013/041444 A1 | 3/2013 |

* cited by examiner

MEASUREMENT SYSTEM AND MEASUREMENT METHOD

BACKGROUND OF THE INVENTION

Field of the Invention

The present invention relates to a golf swing measurement technique.

Description of the Related Art

There have been proposed techniques to analyze a swing for swing improvement of a golfer (for example, Japanese Patent Laid-Open No. 2014-073313, Japanese Patent Laid-Open No. 2014-530047, Japanese Patent Laid-Open No. 2011-502602, Japanese Patent Laid-Open No. 2015-096105, Japanese Patent Laid-Open No. 2014-073314, Japanese Patent Laid-Open No. 2011-030761, Japanese Patent Laid-Open No. 2013-090862, Japanese Patent Laid-Open No. 2009-005760, Japanese Patent Laid-Open No. 2008-539856, and Japanese Patent Laid-Open No. 3-012183). For example, Japanese Patent Laid-Open No. 2014-073313 discloses a system in which inertial sensors are attached to the upper body of a golfer and a golf club to analyze the kinetic energies of the golfer and the golf club based on the detection results. Additionally, Japanese Patent Laid-Open Nos. 2014-530047 and 2011-502602 each disclose a system that performs swing analysis by using a force plate (also referred to as floor reaction force measurement device or a foot pressure measurement device).

One of the motivations of a golfer to improve his/her swing is to increase the carry of a shot. To increase the carry of a shot, the energy released by the golfer during a swing needs to be used efficiently to strike the golf ball via a golf club. While it is necessary to consider the energy released from the entire body of the golfer during a swing in order to evaluate the energy efficiency, it is preferable to measure the energy released from the entire body in a comparatively simple manner.

SUMMARY OF THE INVENTION

It is an object of the present invention to measure the energy of the swing released from the entire body of the golfer at strike in a comparatively simple manner.

According to the present invention, there is provided a measurement system comprising: a first measurement unit configured to measure floor reaction forces of golfer's left and right legs; a second measurement unit that is attached to an upper body of a golfer and configured to measure an angular velocity of the golfer; and a processing unit, wherein the processing unit calculates, based on measurement results of the first measurement unit and the second measurement unit, a first energy which is a kinetic energy of the golfer during a swing.

According to the present invention, there is provided a measurement method comprising: obtaining each measurement result of a first measurement configured to measure floor reaction forces of golfer's left and right legs and a second measurement unit that is attached to an upper body of a golfer and configured to measure an angular velocity of the golfer; and calculating, based on the measurement results of the first measurement unit and the second measurement unit, a first energy which is a kinetic energy of the golfer during a swing.

Further features of the present invention will become apparent from the following description of exemplary embodiments (with reference to the attached drawings).

DESCRIPTION OF THE EMBODIMENTS

<System Arrangement>

Figure 1:
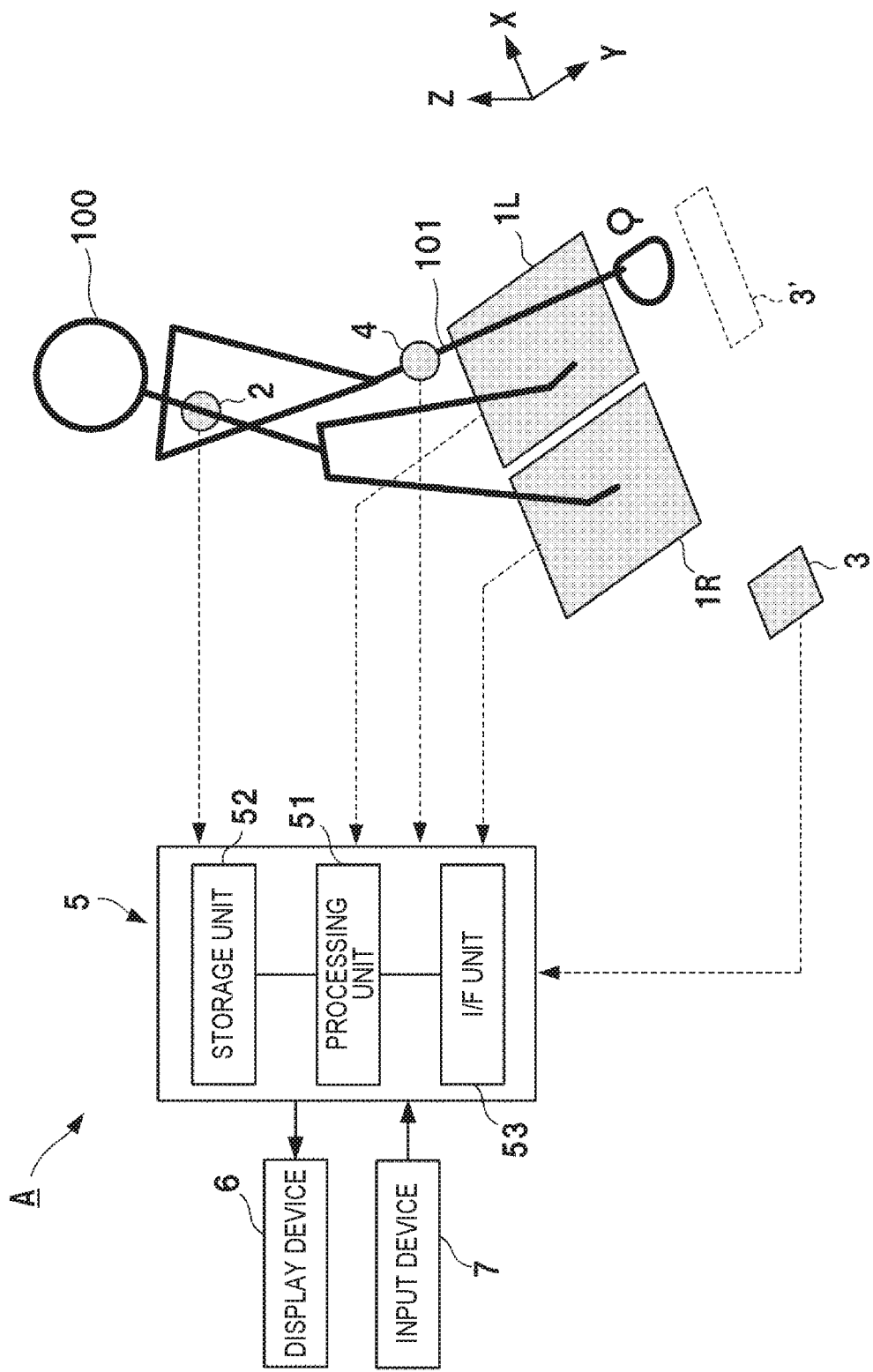
FIG. 1 is a schematic view of a measurement system according to an embodiment of the present invention.

FIG. 1 is a schematic view of a measurement system A according to an embodiment of the present invention. The measurement system A includes a pair of force plates 1R and 1L, measurement units 2, 3, and 4, a processing device 5, a display device 6, and an input device 7. Arrows X, Y, and Z indicate the three-dimensional coordinate system of a testing area of the measurement system A, and the force plates 1R and 1L and the measurement units 2 to 4 are provided in correspondence with this coordinate system. The arrows X and Y indicate horizontal directions perpendicular to each other, and the arrow Z indicates the vertical direction. The arrow X is set in the ball line direction of a golf ball.

The force plates 1R and 1L form measurement units that measure the floor reaction forces of a golfer's left and right legs. The force plates 1R and 1L are arranged side by side in the X direction. The force plate 1R is intended to measure the floor reaction force of the golfer's right leg, and the force plate 1L is intended to measure the floor reaction force of the golfer's left leg. A golfer 100 who is to be measured places his/her right leg on the force plate 1R and his/her left leg on the force plate 1L. In the following description, the force plates 1R and 1L will be called the force plates 1 when there is no need to distinguish between them.

Note that, in this embodiment, the pair of force plates 1R and 1L is used in correspondence with the right and left legs of the golfer. However, it is possible to adopt a single force plate capable of measuring the floor reaction forces of the right and left legs.

Figure 2A:
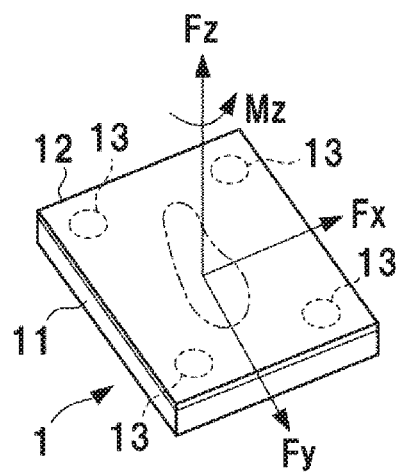
FIGS. 2A, 2B, 2C, and 2D are explanatory views of a force plate, center of feet pressures, position of center of gravity, and an angular velocity about a horizontal axis, respectively.

Each force plate 1 may be any kind of a device as long as it is capable of measuring the translational forces in the three axis directions of X, Y, and Z, and the moment about the Z-axis. FIG. 2A is a schematic view showing an example of the force plate 1. The force plate 1 is formed by arranging a plurality of load sensors 13 between a main body 11 and a foot plate 12, and translational forces Fx, Fy, and Fz in the three axis directions, and a moment Mz about the Z-axis are obtained from the detection results of the plurality of load sensors 13.

Figure 2B:
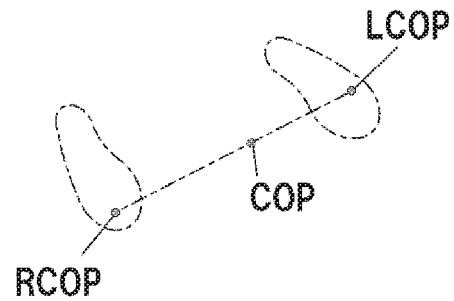

Each force plate 1 can also derive the position of the center of pressure and its magnitude from the detection results of the plurality of sensors load sensors 13. As shown in FIG. 2B, assume that RCOP is a center of pressure of the right leg detected by the force plate 1R, and LCOP is a center of pressure of the left leg detected by the force plate 1L. A center of pressure COP representing both legs as a whole can be calculated from the positions and the magnitudes of the centers of pressure RCOP and LCOP. The center of pressure COP is a position corresponding to the size ratio between the centers of pressure RCOP and LCOP on the line that connects the centers of pressure RCOP and LCOP. If the centers of pressure RCOP and LCOP are the same in size, the center of pressure COP will be at midpoint. If the center of pressure RCOP is larger in size, the position of the center of pressure COP will be biased toward the side of the center of pressure RCOP.

Figure 2C:
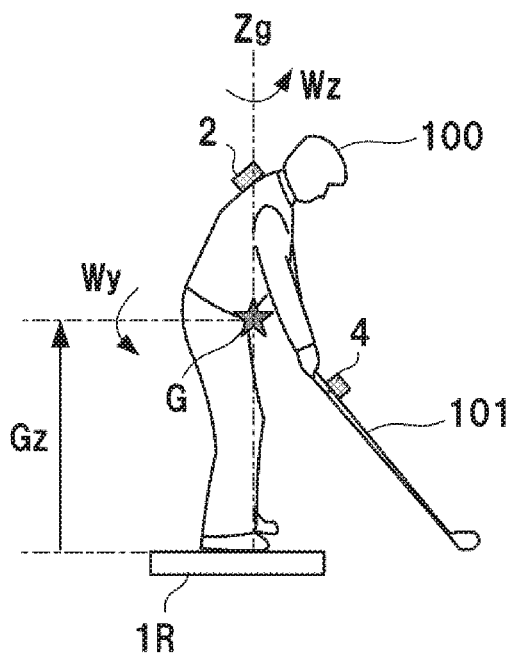

The description returns to FIG. 1. The measurement unit 2 includes at least an angular velocity sensor. For example, as the measurement unit 2, TSND121 of ATR-Promotions can be used. The measurement unit 2 is attached to the upper body of the golfer 100, for example, on the torso between the hip and the shoulders, at a position where the upper body rotation of the golfer 100 can be measured. Although the measurement unit is attached to the upper portion of the golfer's back in the example of FIG. 1, the unit may be attached to the chest side. The measurement unit 2 measures an angular velocity Wz about the Z-axis which passes through the center of gravity of the golfer 100 (more accurately, the center of gravity of a golf club 101 and the golfer 100 holding the club) during a swing. FIG. 2C is a view explaining this measurement. In FIG. 2C, a center of gravity G of the golfer 100 during a swing and a line Zg as the Z-axis which passes through the center of gravity G are shown. When the measurement unit 2 is attached to the upper body of the golfer 100, as shown in FIG. 2C, the measurement unit 2 is positioned at a position on or close to the line Zg. Hence, the detection result of the measurement unit 2 can be regarded as the angular velocity Wz about the Z-axis which passes through the center of the gravity of the golfer 100 during the swing.

The position of the center of gravity G changes during the swing. The position of the center of gravity G can be calculated, for example, in the following manner. Let the position of the center of gravity G when the golfer 100 is still at the time of address be the initial position. This makes it possible to calculate the change amounts in the X-, Y-, and Z-directions of the center of the gravity G from the translational forces Fx, Fy, and Fz in the three axis directions detected by the force plates 1 (total value of the right and left force plates 1R and 1L). That is, in an equation of motion: m×a=F, the total mass of the golfer 100 and the golf club 101 is substituted in a mass m of the body of motion and the translational forces detected by the force plates 1 are substituted in F, thereby obtaining an acceleration a. A speed is derived from the integrated value of the acceleration a, and a position is calculated by the integrated value of the speed.

In a static state, the x- and y-direction positions of the center of gravity G and those of the center of pressure COP match. In a dynamic state, they may not match. Of the initial positions of the center of gravity G, the X- and y-direction positions can be set as the center of pressure COP when the golfer 100 is still at the time of address. The initial position (height Gz) in the Z direction shown in FIG. 2C cannot be measured by the system A of this embodiment. Thus, it may be set as a fixed value (for example, 90 cm). Alternatively, it may be set based on the height of the golfer 100. For example, it may be a value that is 50% to 60% of the golfer's height. As a result, the initial position in the Z direction of the center of gravity G can be conveniently set without greatly reducing the calculation accuracy.

Figure 2D:
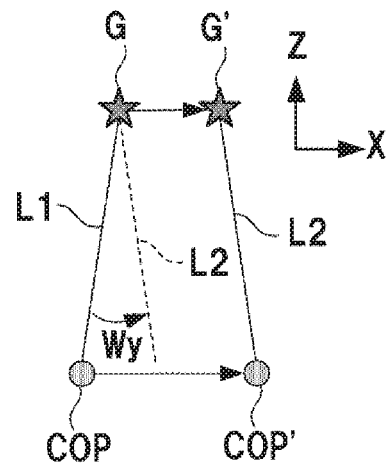

Although the angular velocity Wz about the Z-axis passing through the center of gravity G of the golfer 100 is detectable by the measurement unit 2 as described above, an angular velocity Wy about the Y-axis passing through the center of gravity G shown in FIG. 2C can be derived from the detection results of force plates 1. FIG. 2D is a view explaining this derivation.

FIG. 2D shows a case in which the position of the center of gravity G has changed to a center of gravity G' and the position of the center of pressure COP has changed to a center of pressure COP' on the X-Z plane in the minute time of a swing. A line L1 is a virtual line connecting the center of gravity G and the center of pressure COP, and a line L2 is a virtual line connecting the center of gravity G' and the center of pressure COP'. As shown in FIG. 2D, the angular velocity Wy can be specified as the relative angular velocity of the center of pressure COP with respect to the center of gravity G on the X-Z plane.

The description returns to FIG. 1. The measurement unit 3 measures the head speed of the golf club 101. In the example of FIG. 1, the measurement unit 3 is a ball flight measurement device arranged in the back of the ball line with respect to the golf ball that is to be struck. For example, TRACKMAN of TRACKMAN can be used as such a measurement device. The measurement unit 3 can be any kind of a device as long as it can measure the head speed of the golf club 101. For example, it may be a measurement unit that is arranged in front of the golfer near the golf ball to be struck and measures the passage of the golf club head and the passage time as that shown as a measurement unit 3' in FIG. 1. It may also be a measurement device that is attached to the golf club 101.

The measurement unit 4 includes an inertial sensor (at least either an acceleration sensor or an angular velocity sensor) and is attached to the grip or the shaft of the golf club 101. For example, TSND121 of ATR-Promotions can be used as the measurement unit 4. The impact timing is specified by the detection result of the measurement unit 4. The acceleration or the angular velocity of the golf club 101 rapidly changes at the time of impact. Hence, the timing of a peak in the change of the detection result of the measurement unit 4 can be set as the impact timing.

The processing device 5 can be formed from a general personal computer. The processing device 5 includes a processing unit 51, a storage unit 52, and an I/F unit (interface unit) 53 that are electrically connected to each other. The processing unit 51 is a processor such as a CPU. The storage unit 52 includes one or a plurality of storage devices. The storage device is, for example, a RAM, a ROM, a hard disk, or the like. Programs to be executed by the processing unit 51 and various types of data are stored in the storage unit 52. Each program to be executed by the processing unit 51 can be configured from a plurality of instructions readable by the processing unit 51.

The I/F unit 53 inputs and outputs data between an external device and the processing unit 51. The I/F unit 53 can include an I/O interface and a communication interface. The measurement units 2 to 4 are communicably connected to the processing device 5 by wired communication or wireless communication, and their detection results are obtained by the processing device 5.

The display device 6 and the input device 7 are connected to the processing device 5. The display device 6 is, for example, an electronic image display device such as a liquid crystal display device and displays the processing result of the processing device 5. The input device 7 is a mouse and a keyboard and is used by the measurer to input data and instruct an operation to the processing device 5.

Measurement Processing Example

Figure 3:
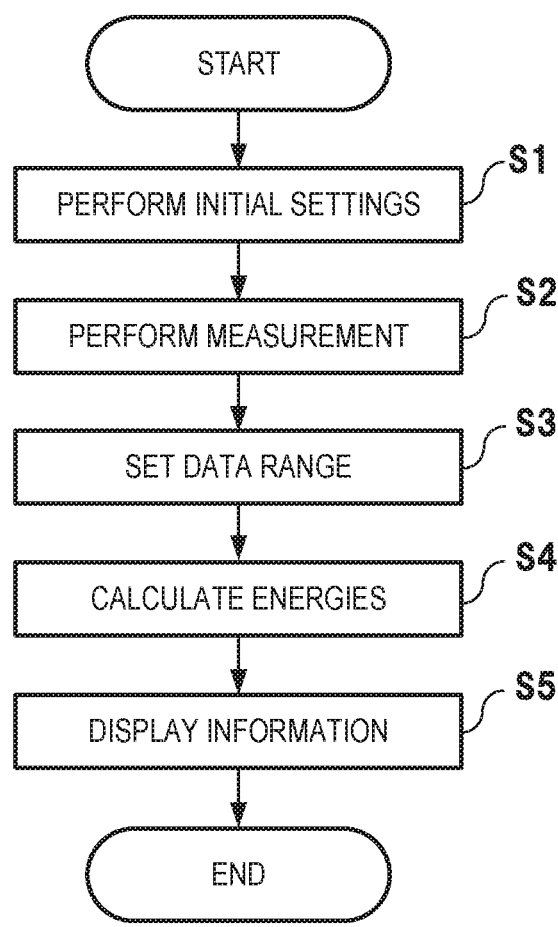
FIG. 3 is a flowchart showing an example of processing executed by a processing device.

An example of a measurement processing program executed by the processing unit 51 will be described with reference to FIG. 3. FIG. 3 is a flowchart of the measurement processing program. In this embodiment, the golfer 100 uses the golf club 101 to make a test shot of the golf ball. Accordingly, the kinetic energy of the golfer 100 during the swing and the kinetic energy of the golf club head are calculated. The former is called a golfer energy and the latter is called a head energy.

The golfer energy is the energy released from the entire body of the golfer during a swing. In this embodiment, as it will be described below, the golfer energy can be derived from the measurement results of two measurement devices, the force plates 1 and the measurement unit 2. Hence, a comparatively simple system arrangement can be used to derive the golfer energy, and the energy of the swing released from the entire body of the golfer at strike can be measured in a comparatively simple manner.

In addition, by calculating the golfer energy and the head energy, the energy efficiency of the golfer's swing at strike can be evaluated.

For example, if the head energy is very small with respect to the golfer energy, it can be understood that the kinetic energy of the golfer is not being efficiently converted to the motion of the golf club head. That is, it can be analyzed that there are many unnecessary movements or that there is a problem in the way the club is swung. Also, if the carry of the golf ball due to a strike is short, it is possible to analyze whether this is due to the physical fitness of the golfer 100 or due to his/her swing.

Initial settings are performed in step S1. In this step, conditions necessary to calculate the golfer energy and the head energy are set. For example, the total of the mass of the golfer 100 and the mass of the golf club 101 is set as the mass of the body of motion of the golfer energy, and this is measureable by the force plates 1. The mass of the head of the golf club 101 is set as the mass of the body of motion of the head energy, and this may be obtained by actual measurement or may be a fixed value (for example, 200 g) if it is not a special head. In addition, the initial position in the Z direction of the center of gravity G described in FIG. 2C is set.

When the initial settings are complete, the golfer 100 prepares to strike the golf ball. Together with the start of measurement in step S2, the golfer 100 stands on the force plates 1 and strikes the golf ball. The measurement results (measurement data) of the respective measurement units 2 to 4 per minute time are obtained and saved from the start of measurement. The storage unit 52 can be used as the destination to save the measurement results. Alternatively, the measurement results may be saved in a data logger provided outside the processing device 5. The measurement is made for a necessary amount of time from when the golfer 100 starts the swing until its end. The end of measurement can be set by time or by the operation of the measurer.

In step S3, of the measurement data obtained in step S2, the range of the data to be used for energy calculation is set. Although all of the measurement data obtained in step S2 can be used for energy calculation, this may be inefficient in some cases. In this embodiment, the impact timing is specified from the measurement data of the measurement unit 4, and pieces of measurement data other than those from a predetermined period before and after the impact timing are excluded as a calculation target.

The predetermined period can be from, for example, two seconds before the impact timing to one second after the impact timing. The kinetic energy released from the golfer 100 from take back till impact becomes most important when evaluating the energy efficiency of a golfer's swing at the time of a strike. By including the measurement data from two seconds before the impact timing, the energy released by the golfer 100 at take back and down swing can be calculated more accurately.

In addition, including the measurement data from two seconds before the impact timing in the calculation target allows the measurement data when the golfer 100 is in a still state (at address) to be included. The center of pressure COP when the golfer 100 is still is set as the initial position of the X- and Y-direction positions of the center of gravity G.

On the other hand, inclusion of the measurement data from one second after the impact timing allows the kinetic energy released by the golfer 100 at follow through to be included as a calculation target. This increases the range of the measurement data which is set as a calculation target in consideration of impact timing measurement error and the like. However, in general, since the kinetic energy released by the golfer 100 at follow through is small, it can be said that its influence on the calculation result of the golfer energy is small.

The highest head speed is used as the head energy. Since the head speed is normally highest immediately before impact, the highest head speed measured by the measurement unit 3 can be used in the above described predetermined period.

Next, in step S4 a golfer energy E1 and a head energy E2 are calculated from the measurement data included in the data range set in step S3.

The head energy E2 is calculated by $$E2 = \tfrac{1}{2} * mh * v^2$$

where v is the highest head speed measured by the measurement unit 3, and mh is the mass of the golf club head.

The golfer energy E1 is the total value of translational energies and rotational energies. FIGS. 4A to 4C, 5A to 5C, 6A, and 6B are explanatory views of formulas. Each formula to be described below assumes a case in which the arrow directions in each drawing have positive values and the opposite directions have negative values unless stated otherwise.

Figure 4A:
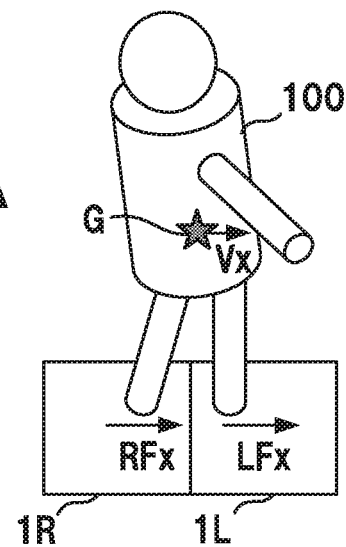
FIGS. 4A to 4C are explanatory views of calculation examples of kinetic energies.
Figure 4B:
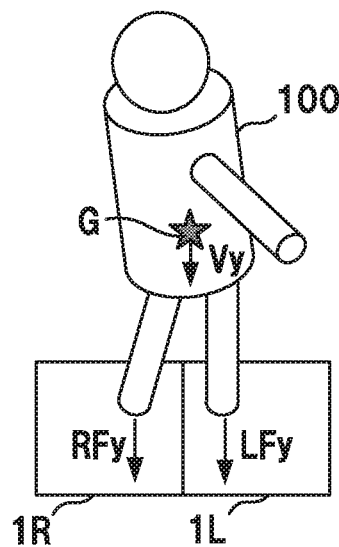
Figure 4C:
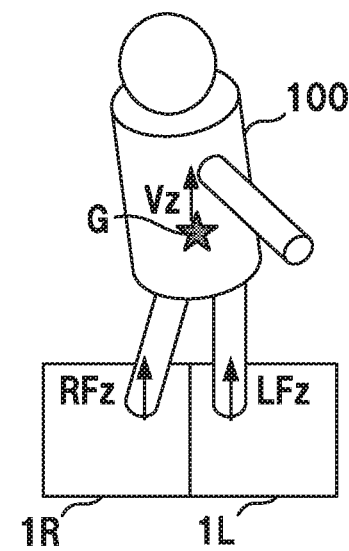

FIGS. 4A to 4C are explanatory views of the formulas of translational energies in the X, Y, and Z directions. A translational energy Ex in the X direction is calculated by $$Ex = \int (RFx + LFx) * Vx \, dt$$

where RFx is the floor reaction force in the X direction of the right leg measured by the force plate 1R, and LFx is the floor reaction force in the X direction of the left leg measured by the force plate 1L. Vx is the traveling speed in the X direction of the center of gravity G.

A translational energy Ey in the Y direction is calculated by $$Ey = \int (RFy + LFy) * Vy \, dt$$

where RFy is the floor reaction force in the Y direction of the right leg measured by the force plate 1R, and LFy is the floor reaction force in the Y direction measured by the force plate 1L. Vy is the traveling speed in the Y direction of the center of gravity G.

A translational energy Ez in the Z direction is calculated by $$Ez=\int(RFz+LFz-m^*g)^*Vzdt$$

where RFz is the floor reaction force in the Z direction of the right leg measured by the force plate 1R, and LFz is the floor reaction force in the Z direction of the left leg measured by the force plate 1L. m is the total mass of the golfer 100 and the golf club 101, and g is the gravitational acceleration. Vz is the traveling speed in the Z direction of the center of gravity G.

Figure 5A:
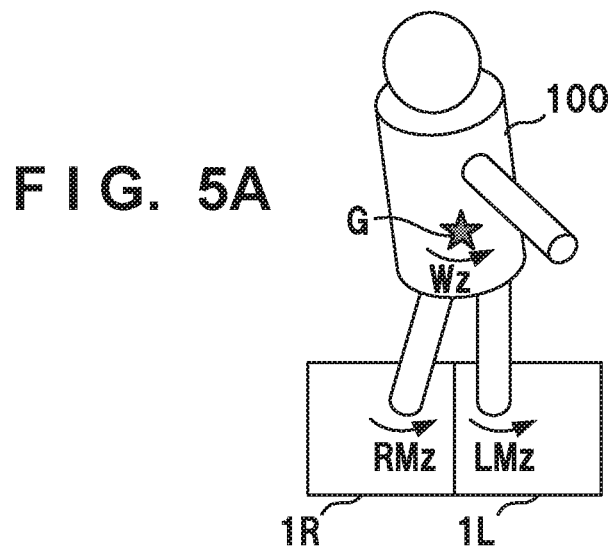
FIGS. 5A to 5C are explanatory views of calculation examples of kinetic energies.

FIGS. 5A to 5C, 6A, and 6B are explanatory views of rotational energy formulas. FIG. 5A is an explanatory view of a rotational energy $Ew_1$ about the Z-axis generated by the torque of the legs of the golfer 100. The rotational energy $Ew_1$ is calculated by $$EW_1=\int(RMz+LMz)^*Wzdt$$

where RMz is the moment about the Z-axis of the right leg measured by the force plate 1R, and LMz is the moment about the Z-axis of the left leg measured by the force place 1L. Wz is the angular velocity about the Z-axis passing through the center of gravity G measured by the measurement unit 2.

Figure 5B:
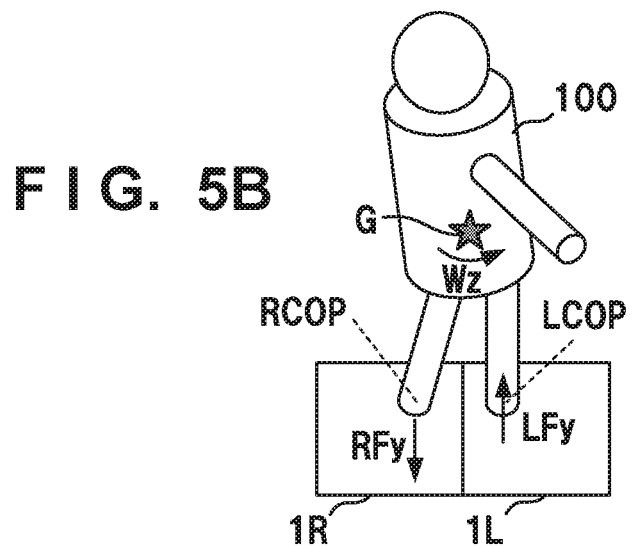

FIG. 5B is an explanatory view of a rotational energy $Ew_2$ about the Z-axis generated by the translational forces of the legs of the golfer 100. Rotational energy $Ew_2$ is calculated by $$Ew_2=\int[(LFy^*Lx+RFy^*Rx)^*Wzdt$$

where LFy, RFy, and Wz are the same as those already described above. Lx is the X-direction distance between the position of the center of gravity G and the center of pressure LCOP of the left leg. Rx is the X-direction distance between the position of the center of gravity G and the center of pressure RCOP of the right leg.

Figure 5C:
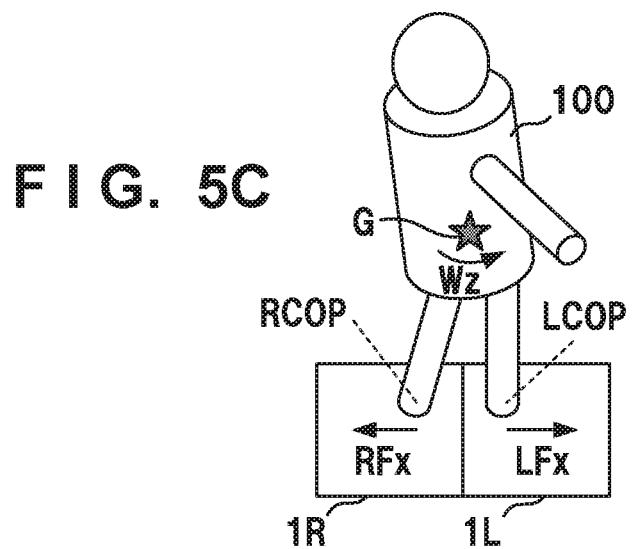

FIG. 5C is an explanatory view of a rotational energy $Ew_3$ about the Z-axis generated by the translational forces of the legs of the golfer 100. The rotational energy $Ew_3$ is calculated by $$Ew_3=\int(LFy^*Ly+RFy^*Ry)^*Wzdt$$

where LFy, RFy, and Wz are the same as those already described above. Ly is the Y-direction distance between the position of the center of gravity G and the center of pressure LCOP of the left leg. Ry is the Y-direction distance between the position of the center of gravity G and the center of pressure RCOP of the right leg. Ly and Ry will have positive values if they are located more toward the front with respect to the center of gravity, otherwise they will have negative values.

Figure 6A:
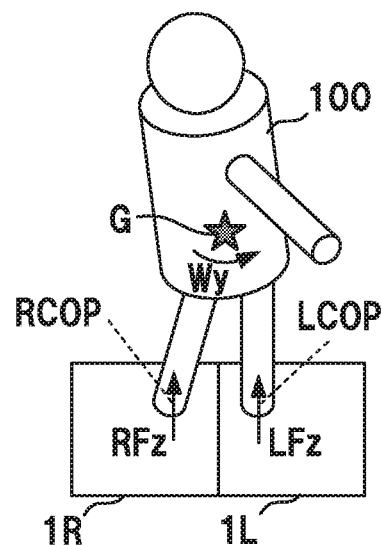
FIGS. 6A and 6B are explanatory views of calculation examples of kinetic energies.

FIG. 6A is an explanatory view of a rotational energy $Ew_4$ about the Y-axis generated by the translational forces of the legs of the golfer 100. The rotational energy $Ew_4$ is calculated by $$Ew_4=\int\{[((RFz+LFz)-m^*g)^*LFz/(RFz+LFz)]^*Lx-[((RFz+LFz)-m^*g)^*RFz/(RFz+LFz)]^*Rx\}^*Wydt$$

where LFz, Lx, RFz, Rx, m, and g are the same as those already described above. Wy is the angular velocity about the Y-axis passing through the center of gravity G and is the same as that explained with reference to FIG. 2D.

Figure 6B:
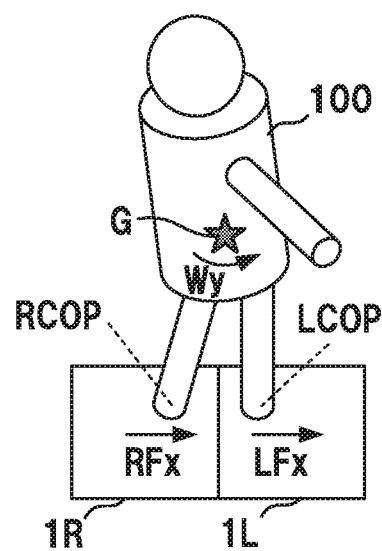

FIG. 6B is an explanatory view of a rotational energy $Ew_5$ about the Y-axis generated by the translational forces of the legs of the golfer 100. The rotational energy $Ew_5$ is calculated by $$Ew_5=\int(LFx+RFx)^*GH^*Wydt$$

where LFx, RFx, and Wy are the same as those already described above. GH is the position (the height from the force plates 1) in the Z direction of the center of gravity G.

From the above calculations, the golfer energy E1 is $E1=Ex+Ey+Ez+Ew_1+Ew_2+Ew_3+Ew_4+Ew_5$.

Figure 7A:
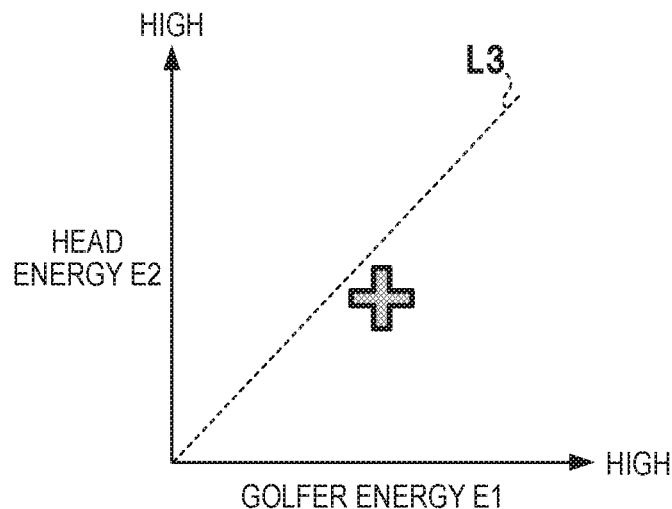
FIGS. 7A and 7B are views showing display examples of a display device.
Figure 7B:
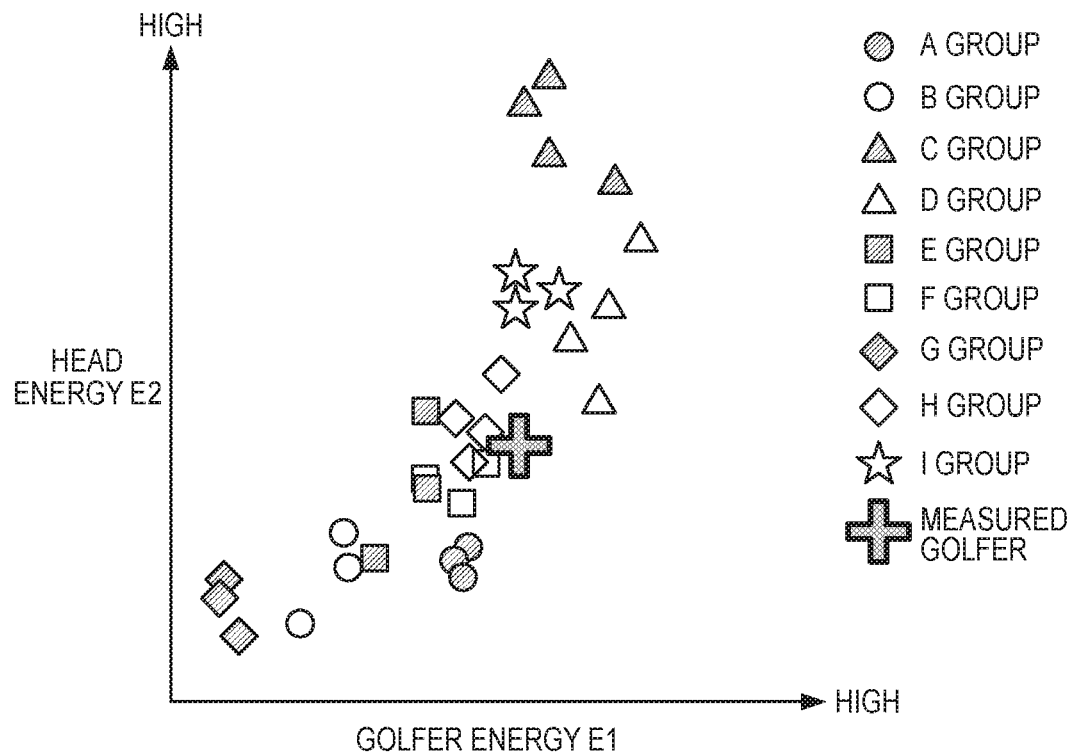

The description returns to FIG. 3. In step S5, the calculation results of step S4 are displayed on the display device 6. FIGS. 7A and 7B show display examples of the calculation results of the golfer energy E1 and head energy E2.

The example of FIG. 7A plots the calculation results from step S4 on a two-dimensional graph having the golfer energy E1 as the abscissa and the head energy E2 as the ordinate. Note that relation between the abscissa, the ordinate, and the types of energy can be reversed. This allows the golfer 100 who was subjected to the measurement to understand the relation between his/her golfer energy E1 and the head energy E2.

In the example of FIG. 7A, a line L3 which serves as a criterion of energy efficiency is also displayed. The line L3 is, for example, a line that indicates the average relation between the golfer energy E1 and the head energy E2. If the plot is located more on the upper left side with respect to the line L3, it indicates that the golfer 100 who was subjected to the measurement has comparatively high swing efficiency, and if the plot is located more on the lower right side with respect to the line 3, it indicates that the swing efficiency is comparatively low. The golfer 100 who was subjected to the measurement can use this as a criterion for swing improvement.

The example of FIG. 7B displays, as comparative information, the golfer energy E1 and head energy E2 data of a plurality of golfers that were measured in the past together with the energy calculation result of the golfer 100 who was subjected to the measurement. Comparison between his/her data with the data of other golfers allows the golfer 100 who was subjected to the measurement to have criteria for swing improvement. The data of the plurality of golfers that were measured in the past can be stored in the storage unit 52.

Each piece of data of the plurality of golfers that were measured in the past is associated with an attribute, and its plot has a different form for each attribute. In the example of FIG. 7B, the attributes have been divided into groups A to I. Each attribute can be, for example, one or a combination of sex, age, handicap, professional/amateur, height, and weight.

The golfer 100 who was subjected to the measurement can compare, for example, his/her data with the data of a plurality of golfers that have the same attribute and use it as a criterion for swing improvement. At this time, it may be set so that only the data of golfers of a specific attribute are selectively displayed. For example, of groups A to I, it may be set so that the data of the golfers of group A and the data of the golfer 100 who was subjected to the measurement are displayed.

In addition, by comparing his/her data with the data of a plurality of golfers of different attributes, the golfer 100 who was subjected to the measurement can learn about, for example, the technique levels and physical fitness levels of professional golfers and advanced players.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2016-032417, filed Feb. 23, 2016, which is hereby incorporated by reference herein in its entirety.

What is claimed is:

1. A measurement system comprising:
a first measurement unit configured to measure floor reaction forces of golfer's left and right legs;
a second measurement unit that is an angular velocity sensor attached to an upper body of a golfer and configured to measure an angular velocity of the golfer; and
a processing unit,
wherein the processing unit calculates, based on measurement results of the first measurement unit and the second measurement unit, a first energy which is a kinetic energy of the golfer during a swing,
the first energy includes a translational energy and a rotational energy of the golfer,
the translational energy is calculated based on the measurement result of the first measurement unit, and
the rotational energy is calculated based on the measurement results of the first measurement unit and the second measurement unit.

2. The system according to claim 1 further comprising a third measurement unit configured to measure a head speed of the golf club,
wherein the processing unit calculates, based on a measurement result of the third measurement unit, a second energy which is a kinetic energy of a golf club head.

3. The system according to claim 2 further comprising a storage unit configured to store pieces of information about the first energy and the second energy of a plurality of golfers; and
a display unit configured to display comparison information comparing the first energy and the second energy calculated by the processing unit and the pieces of information stored in the storage unit.

4. The system according to claim 3, wherein the comparison information is a graph in which one of the abscissa and the ordinate is set as the first energy and the other is set as the second energy.

5. The system according to claim 1, wherein the rotational energy is calculated based on a position of a center of gravity of the golfer, and
of initial positions of the center of gravity, an initial position in a horizontal direction is set based on the measurement result of the first measurement unit and an initial position in a vertical direction is a fixed value.

6. The system according to claim 1, wherein the rotational energy is calculated based on a position of a center of gravity of the golfer, and
of initial positions of the center of gravity, an initial position in a horizontal direction is set based on the measurement result of the first measurement unit, and an initial position in a vertical direction is set based on the height of the golfer.

7. The system according to claim 1, wherein the translational energy includes energies in three axis directions, and
the rotational energy includes an energy about a horizontal axis and an energy about a vertical axis passing through a center of gravity of the golfer.

8. The system according to claim 1 further comprising an inertial sensor which is to be attached to a golf club,
wherein the processing unit specifies an impact timing based on a detection result of the inertial sensor, and
the first energy is calculated based on measurement results of the first measurement unit and the second measurement unit obtained from a predetermined period before and after the impact timing.

9. A measurement method comprising:
obtaining each measurement result of a first measurement configured to measure floor reaction forces of golfer's left and right legs and a second measurement unit that is an angular velocity sensor attached to an upper body of a golfer and configured to measure an angular velocity of the golfer; and
calculating, based on the measurement results of the first measurement unit and the second measurement unit, a first energy which is a kinetic energy of the golfer during a swing,
the first energy includes a translational energy and a rotational energy of the golfer,
the translational energy is calculated based on the measurement result of the first measurement unit, and
the rotational energy is calculated based on the measurement results of the first measurement unit and the second measurement unit.

10. The system according to claim 1, wherein the first energy is a kinetic energy released from the entire body of the golfer during a swing.

11. The system according to claim 1, wherein the second measurement unit is only one angular velocity sensor.

12. The system according to claim 1, wherein the angular velocity sensor is configured to measure an angular velocity about a vertical axis which passes through a center or a gravity of the golfer during a swing.

* * * * *